(12) United States Patent
Yu et al.

(10) Patent No.: US 9,395,791 B2
(45) Date of Patent: Jul. 19, 2016

(54) HEALTH CARE DEVICE AND POWER MANAGEMENT METHOD THEREFOR

(71) Applicant: Quanta Computer Inc., Tao Yuan Shien (TW)

(72) Inventors: Chih-Hsiung Yu, Taoyuan (TW); Yung-Ming Chung, Changhua County (TW); Hsin-Hsueh Wu, Kaohsiung (TW); Yung-Chih Huang, Taoyuan (TW); Shih-Wei Wang, Changhua County (TW)

(73) Assignee: QUANTA COMPUTER INC., Tao Yuan Shien (TW)

( * ) Notice: Subject to any disclaimer, the term of this patent is extended or adjusted under 35 U.S.C. 154(b) by 707 days.

(21) Appl. No.: 13/790,750

(22) Filed: Mar. 8, 2013

(65) Prior Publication Data

US 2014/0100707 A1    Apr. 10, 2014

(30) Foreign Application Priority Data

Oct. 9, 2012   (TW) .............................. 101137296 A

(51) Int. Cl.
| | | |
|---|---|---|
| *G06F 1/32* | (2006.01) | |
| *G06F 1/16* | (2006.01) | |
| *A61B 5/00* | (2006.01) | |
| *A61B 5/024* | (2006.01) | |
| *A61B 5/0404* | (2006.01) | |

(52) U.S. Cl.
CPC .......... *G06F 1/3231* (2013.01); *A61B 5/02438* (2013.01); *A61B 5/0404* (2013.01); *A61B 5/6805* (2013.01); *A61B 5/6823* (2013.01); *A61B 5/6898* (2013.01); *G06F 1/163* (2013.01); *G06F 1/3278* (2013.01); *G06F 1/3287* (2013.01); *A61B 5/0002* (2013.01); *A61B 2505/09* (2013.01); *G06F 2200/1636* (2013.01); *Y02B 60/126* (2013.01); *Y02B 60/1282* (2013.01); *Y02B 60/1289* (2013.01)

(58) Field of Classification Search
None
See application file for complete search history.

(56) References Cited

U.S. PATENT DOCUMENTS

| | | | | |
|---|---|---|---|---|
| 7,873,772 | B2 * | 1/2011 | Waldhoff | A61B 5/0002 439/38 |
| 8,521,148 | B1 * | 8/2013 | Hohteri | G06F 1/3231 455/418 |
| 2011/0092780 | A1 * | 4/2011 | Zhang | A61B 5/053 600/301 |
| 2013/0072765 | A1 * | 3/2013 | Kahn | A61B 5/01 600/301 |

FOREIGN PATENT DOCUMENTS

| | | |
|---|---|---|
| CN | 200954103 Y | 10/2007 |
| CN | 102018505 A | 4/2011 |
| CN | 102525426 A | 7/2012 |

OTHER PUBLICATIONS

Taiwanese Office Action dated on Oct. 1, 2014.

* cited by examiner

*Primary Examiner* — Sean Shechtman
(74) *Attorney, Agent, or Firm* — Rabin & Berdo, P.C.

(57) ABSTRACT

A power management method for a health care device is included. The method includes: detecting whether a smart garment is in contact with a user body; operating the health care device in a normal mode when the smart garment is in contact with the user body, or operating the health care device in a low-power mode when the smart garment is not in contact with the user body; and under the low-power mode, detecting whether the health care device is tapped to determine whether to transmit user health data to a user device.

7 Claims, 5 Drawing Sheets

HEALTH CARE DEVICE AND POWER MANAGEMENT METHOD THEREFOR

This application claims the benefit of Taiwan application Serial No. 101137296, filed Oct. 9, 2012, the subject matter of which is incorporated herein by reference.

TECHNICAL FIELD

The disclosure relates to a health care device and a power management method therefor.

BACKGROUND

Modern people may often neglect the caring for health as being occupied with busy work, and so various health care products are developed. Through the health care products, health parameters such as blood pressures, blood sugar levels, electrocardiographies, and calorie consumptions can be measured and recorded.

For easy portability, such health care products are usually powered by a battery. Therefore, with a good power management, a powering period of the battery is increased for further enhancing the ease of use.

SUMMARY OF THE DISCLOSURE

The embodiments of the disclosure relate to a health care device and a power management method therefor. By detecting whether a smart garment (with the health care device fixedly attached to the smart garment) comes into contact with a human body, an operating mode of the health care device is determined.

According to an exemplary embodiment of the disclosure, a power management method for a health care device is provided. The health care device includes a leads-off detection unit, a processor, an activity detection unit, and an activity activation detection unit. The power management method includes steps of: detecting by the power activation detection unit whether the health care device is fixedly attached to a smart garment; detecting by the leads-off detection unit whether the smart garment is in contact with a user body; operating the health care device in a normal operating mode when it is determined that the smart garment is in contact with the user body; operating the health care device in a low-power mode when it is determined that the smart garment is not in contact with the user body; and under the low-power mode, detecting by the activity detection unit whether the health care device is tapped to determine whether to transmit user health data to a user device.

According to another exemplary embodiment, a health care device is provided. The health care device includes: a processing unit; a power module, for powering the health care device; a physiological signal measurement unit, coupled to the processing unit, for detecting a user physiological signal; an activity detection unit, coupled to the processing unit, for detecting a user activity and a user tap; a leads-off detection circuit, coupled to the processing unit, for detecting whether a smart garment fixedly attached to the health care device is in contact with a user body; and a wireless communication unit, coupled to the processing unit, for transmitting user health data detected by the health care device to a user device. When the processing unit determines that the smart garment is in contact with the user body, the processing unit controls the health care device to operate in a normal operating mode. When the processing unit determines that the smart garment is not in contact with the user body, the processing unit controls the health care device to operate in a low-power mode.

The above and other aspects of the disclosure will become better understood with regard to the following detailed description of the preferred but non-limiting embodiments. The following description is made with reference to the accompanying drawings.

Figure 1A:
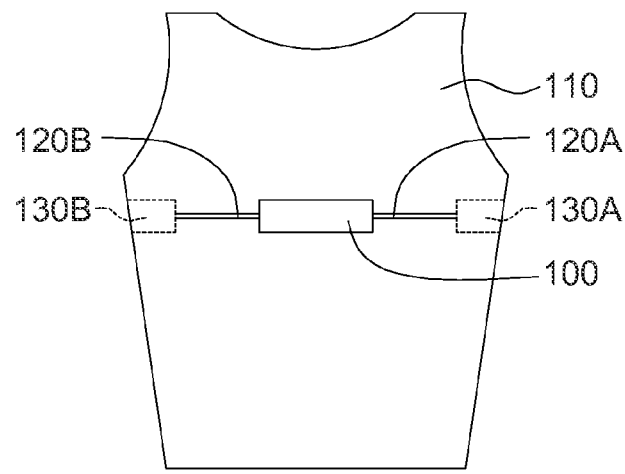
FIG. 1A is a schematic diagram of a health care device according to an embodiment of the disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

DETAILED DESCRIPTION OF THE DISCLOSURE

Figure 1B:
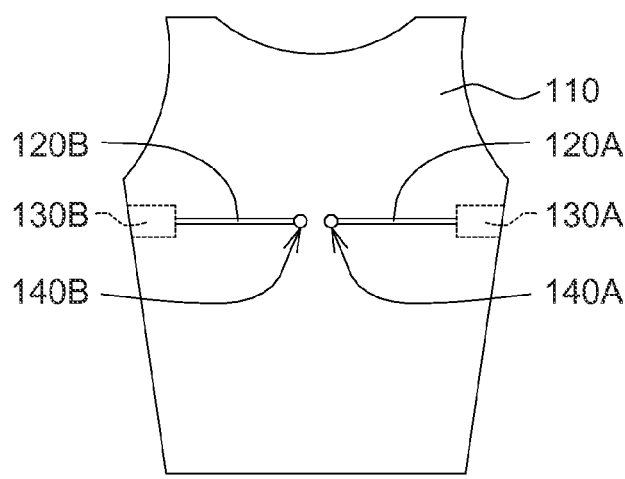
FIG. 1B is a schematic diagram of a smart garment implemented jointly with a health care device according to an embodiment of the disclosure.

FIG. 1A shows a schematic diagram of a health care device according to one embodiment. FIG. 1B shows a schematic diagram of a smart garment implemented jointly with a health care device according to one embodiment. Referring to FIGS. 1A and 1B, a smart garment 110 includes wires 120A and 120B, conductive cloths 130A and 130B, and magnetic snaps 140A and 140B. When two metal contacts (e.g., metal contacts LA and RA in FIG. 2) of the health care device 100 are attracted and engaged by the magnetic snaps 140A and 140B of the smart garment 110, the health care device 100 is fixedly attached to the smart garment 110.

The conductive cloths 130A and 130B of the smart garment 110 come into contact with human skin to transmit a physiological parameter (e.g., an electrocardiography signal) of the user body to the health care device 100 via the wires 120A and 120B as well as the magnetic snaps 140A and 140B. Thus, the health care device 100 may accordingly detect an electrocardiography signal of a human being.

In one embodiment, to efficiently manage power for increasing a powering period of a battery, when a user is not wearing the smart garment 110 while the health care device 100 is fixedly attached to the smart garment, the health care device 100 is capable of detecting that the smart garment 110 is not in contact with a human body (i.e., it is determined that the smart garment 110 is not being worn by a human body), and the health care device 100 then automatically enters a low-power mode.

Further, in another application situation of the health care device 100 according to one embodiment, when the health care device 100 is in a low-power mode, a user may tap the health care device 100 for several times (e.g., twice) if the user wishes to transmit data (e.g., a physiological parameter of a human body) in the health care device 100 to another user device (e.g., a user's cell phone). After detecting the user tap, the health care device 100 automatically supplies power to a wireless communication unit to connect to the cell phone in order to transmit data, so as to provide quick and convenient data management.

Figure 2:
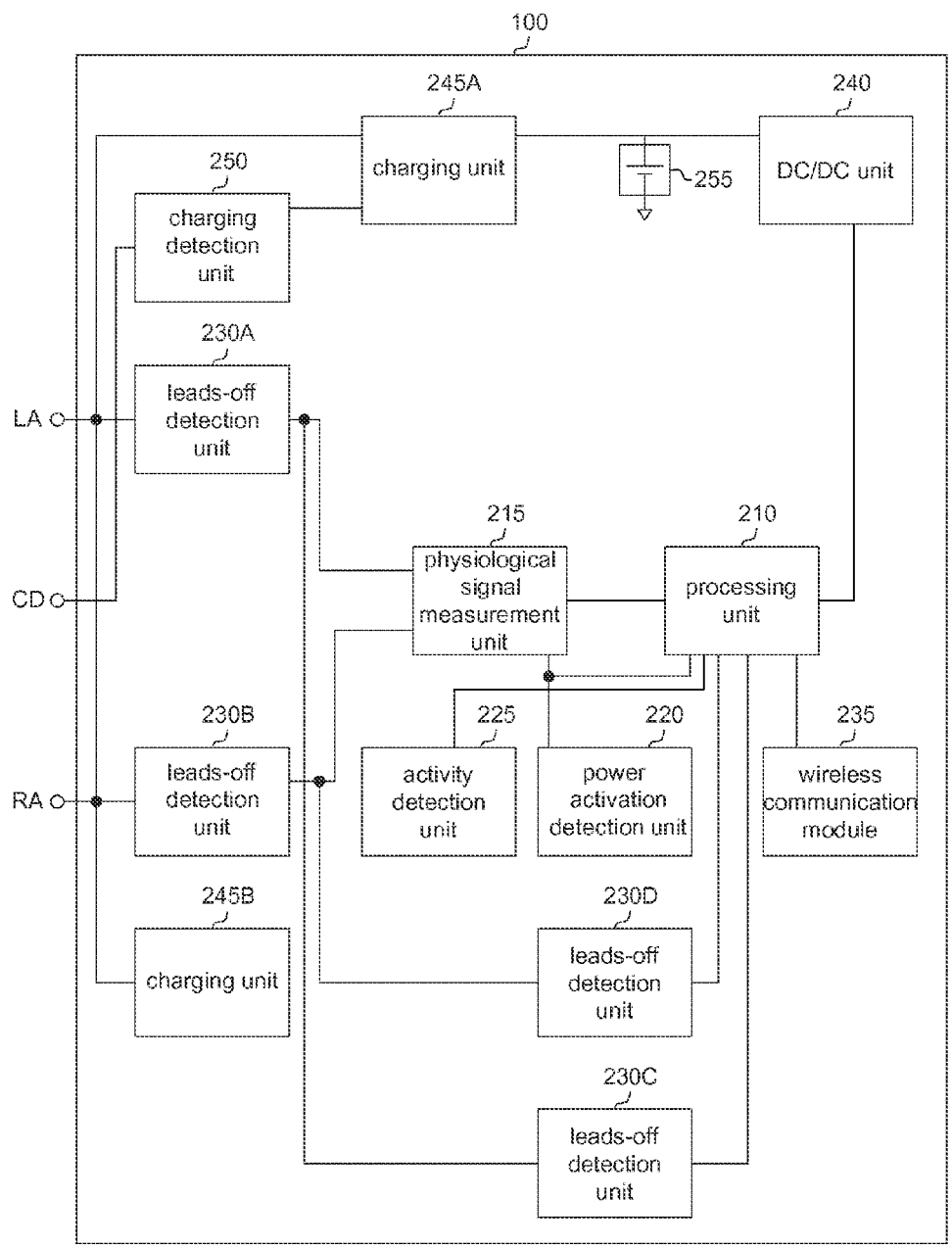
FIG. 2 is a functional block diagram of a health care device according to an embodiment of the disclosure.

Structural details and functions of the health care device 100 are described below. FIG. 2 shows a functional block diagram of the health care device 100 according to one embodiment. As shown in FIG. 2, the health care device 100 is powered by a power source 255 (e.g., a rechargeable battery). The health care device 100 includes a processing unit 210 (e.g., a microprocessor), a physiological signal measurement unit 215, a power activation detection unit 220, an activity detection unit 225, leads-off detection units 230A to 230D, a wireless communication unit 235, a DC/DC unit 240, charging units 245A and 245B, a charging detection unit 250, and metal contacts LA, RA and CD.

The processing unit 210 processes signals transmitted from other units to perform corresponding operations.

The physiological signal measurement unit 215 measures a user physiological signal (e.g., an electrocardiography signal), which is further transmitted to the processing unit 210.

The power activation detection unit 220 detects whether the health care device 100 is fixedly attached to the magnetic snaps 140A and 140B of the smart garment 110. For example, the power activation detection unit 220 includes a magnetic sensor (e.g., a Hall sensor). When the health care device 100 is fixedly attached to the magnetic snaps 140A and 140B of the smart garment 110, the power activation detection unit 220 detects a change in magnetic field due to the magnetic snaps 140A and 140B, and the health care device 100 then enters from a low-power mode to a measuring mode (i.e., a normal mode). That is, the power activation detection unit 220 notifies the physiological signal measurement unit 215 to measure the user physiological signal through the processing unit 210. The low-power mode refers to a mode in which a part of units of the health care device 100, such as the wireless communication unit 235, is deactivated.

The activity detection unit 225 detects a user activity or a user tap. For example, the activity detection unit 225 includes a gravity sensor (G-sensor). When the health care device 100 is "worn" on a user, the activity detection unit 225 detects a user activity (e.g., the number of walking steps), and transmits a detection result to the processing unit 210. According to the detected user activity (e.g., the number of walking steps) detected by the activity detection unit 225 and the physiological signal (e.g., an electrocardiography signal) detected by the physiological signal detection unit 215, the processing unit 210 determines the calories consumed by the user for health management of the user.

On the other hand, under the low-power mode, when the activity detection unit 225 detects a user tap, the activity detection unit 225 transmits the detection result to the processing unit 210 to activate the wireless communication unit 235. Thus, the wireless communication unit 235 transmits the information including the user physiological parameter and calorie consumption detected by the health care device 100 to a remote electronic device (e.g., a cell phone, a personal computer, a laptop computer or a tablet computer), thereby allowing a user to conveniently manage health parameters thereof.

For example, the wireless communication unit 235 may transmit information such as the user physiological parameter and calorie consumption detected by the health care device 100 to a cell phone. For example, the wireless communication unit 235 is a Bluetooth communication unit or a similar wireless communication unit.

The DC/DC unit 240 transforms a DC current supplied by the power source 255 to a DC current suitable for corresponding units.

Operations of the metal contact CD are associated with charging operations. In one embodiment, an external charging module includes three connectors respectively corresponding to the metal contacts LA, RA and CD. When the health care device 100 is placed on the external charging module, the charging detection unit 250 determines whether the health care device 100 is currently placed at the external charging module according to whether the metal contact CD contacts the corresponding connector of the external charging module. Meanwhile, the determination result is transmitted to the charging units 245A and 245B. When the determination result is affirmative, the external charging module transmits external power to the power source 255 via the connectors corresponding to the metal contacts LA and RA. In one embodiment, the charging unit 245B conducts the metal contact RA to a ground terminal.

Figure 3:
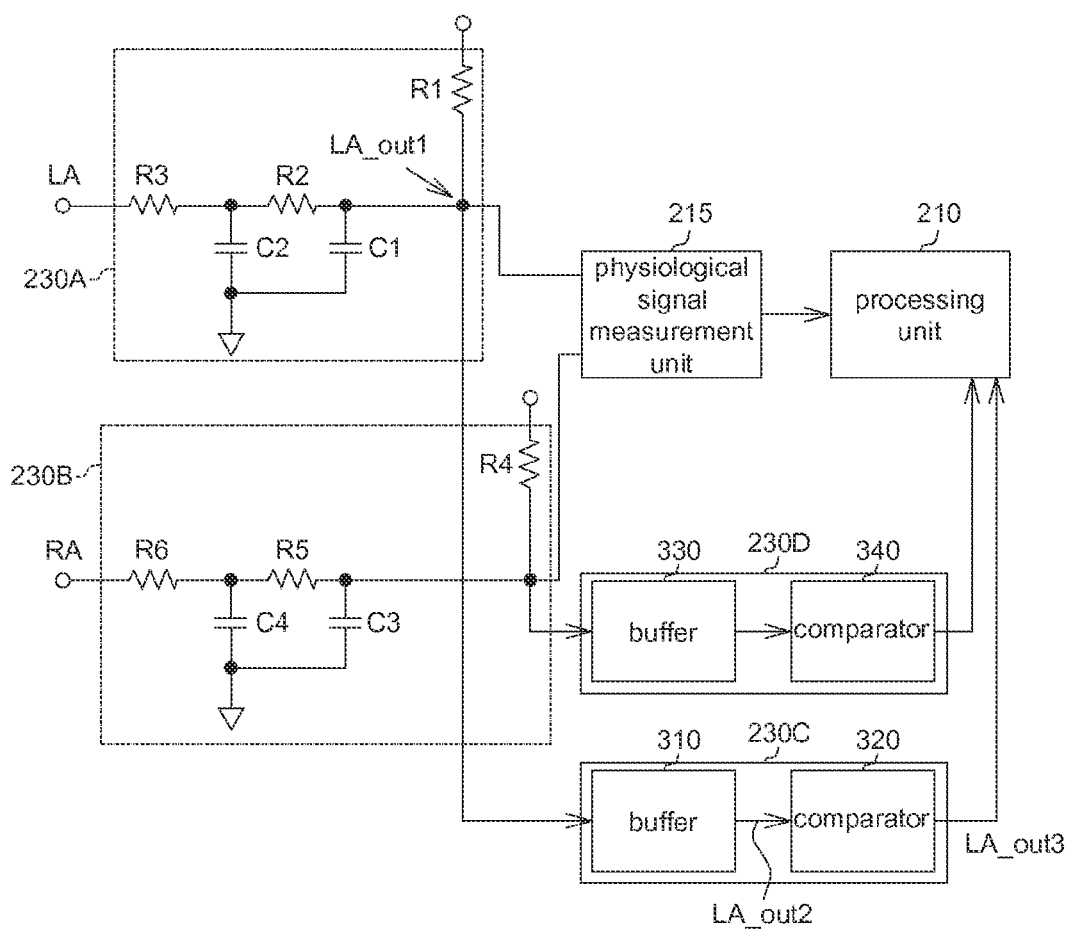
FIG. 3 shows details of leads-off detection units according to an embodiment of the disclosure.

The leads-off detection units 230A to 230D detect whether leads are fallen off, i.e., determine whether the smart garment 110 is worn on a human body. FIG. 3 shows details of the leads-off detection units 230A to 230D according to one embodiment. The leads-off detection unit 230A includes resistors R1 to R3 and capacitors C1 and C2. The leads-off detection unit 230B includes resistors R4 to R6 and capacitors C3 and C4. The leads-off detection unit 230C includes a buffer 310 and a comparator 320. The leads-off detection unit 230D includes a buffer 330 and a comparator 340. It should be noted that above elements forming the leads-off detection units 230A to 230D are examples rather than limitations to the disclosure. To better explain the embodiment, the leads-off detection units 230A and 230C are taken as examples, and a person having ordinary skilled in the art can easily infer operations of the leads-off detection units 230B and 230D.

When the conductive cloth 130A of the smart garment 110 is not in contact with a user body, the wire 120A and the metal contact LA of the smart garment 110 are both floating (regardless of whether the wire 120A and the metal contact LA are electrically connected), and a signal LA_out1 maintains at a high potential (e.g., the signal LA_out1>2V). In contrast, when the conductive cloth 130A of the smart garment 110 is in contact with a user body and the wire 120A is electrically connected to the metal contact LA, an impedance loop is formed, and the signal LA_out1 changes from a high potential to a low potential (e.g., LA_out1<1V).

The signal LA_out1 is coupled to the buffer 310 of the leads-off detection unit 230C. The buffer 310 prevents the measurement of the electrocardiography signal from being affected by a load effect. Further, the buffer 310 outputs a signal LA_out2, which in principle has a same level as that of the signal LA_out1.

The output signal LA_out2 of the buffer 310 is inputted into the comparator 320. The comparator 320 compares the signal LA_out2 with a reference signal to generate a signal LA_out3 to accurately determine whether the metal contact LA is at a floating state (high potential) or a loop state (low potential). In one embodiment, for example, the reference signal is 2V. When the signal LA_out1 (i.e., the signal LA_out2) is at a high potential (in a floating state), e.g., 3.3V, the comparator 320 determines that the signal LA_out2 is greater than the reference signal, and thus outputs a high-potential signal LA_out3 (e.g., 3.3V). When the signal LA_out1 (i.e., the signal LA_out2) is at a low potential (in a loop state), e.g., 1V, the comparator 320 determines that the signal LA_out2 is smaller than the reference signal, and thus outputs a low-potential signal LA_out3 (e.g., 0V or 1V). The processing unit 210 determines whether any lead is fallen off (i.e., determines whether the conductive cloths 130A and 130B are in contact with a human body—whether the smart garment is worn on a human body) according to the output signals of the leads-off detection units 230C and 230D.

In one embodiment, when the signal LA_out3 of either of the leads-off detection units 230C and 230D is at a high potential, e.g., 3.3V, it is determined that the smart garment is not worn on a human body; when the signals LA_out3 of both the leads-off detection units 230C and 230D are at a low potential (e.g., 0V or 1V), the processing unit 210 determines that the smart garment is worn on a human body.

Figure 4:
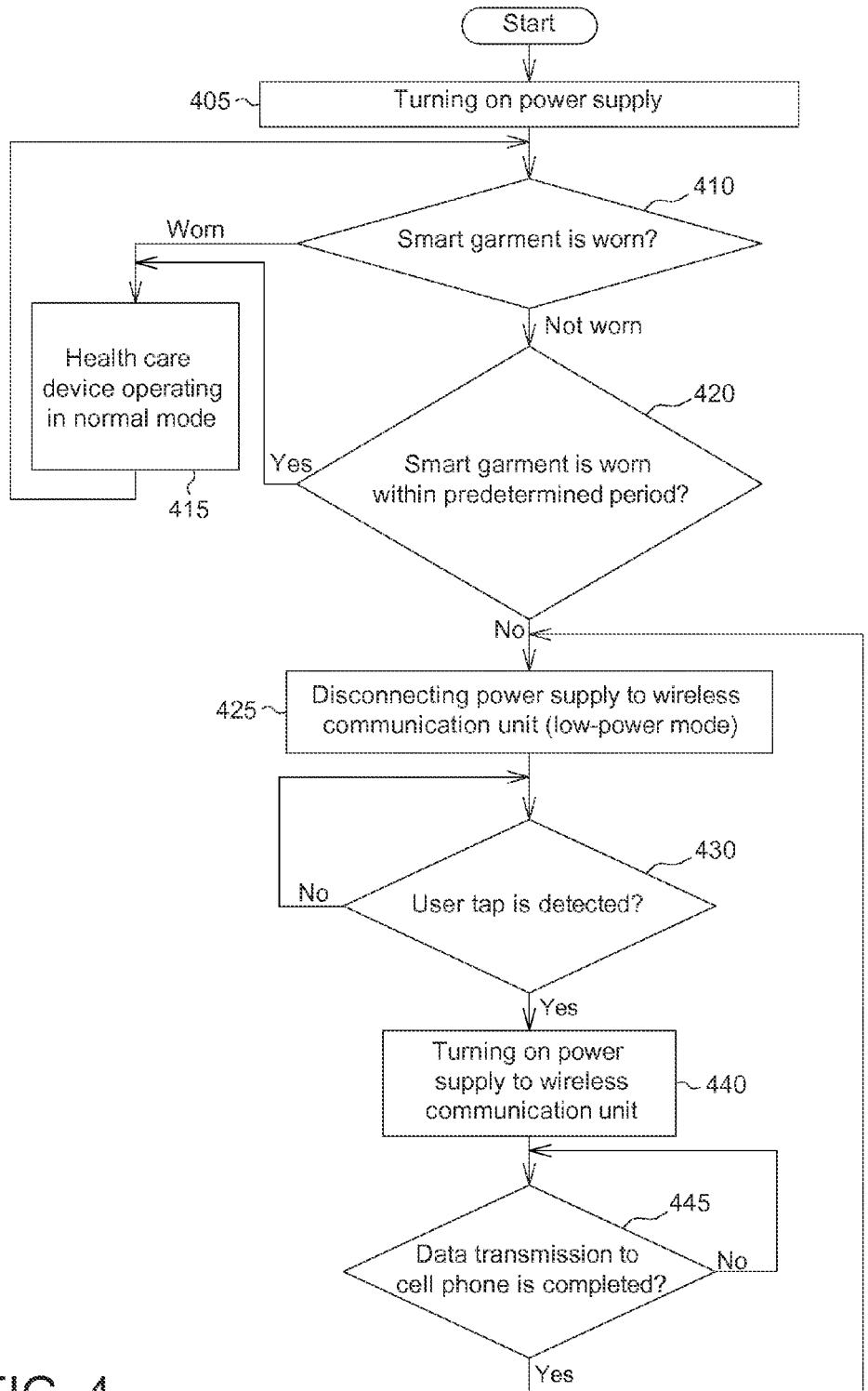
FIG. 4 is a flowchart of a power management method for a health care device according to an embodiment of the disclosure.

FIG. 4 shows a flowchart of a power management method for a health care device according to one embodiment. Referring to FIG. 4, in step 405, a power of the health care device is turned on. In step 410, it is determined whether the smart garment is worn on a human body. Details of step 410 are as given in above descriptions associated with whether any lead is fallen off. It should be noted that, before entering step 410, the health care device 100 is fixedly attached to the smart garment 110 in order to fully exercise the subsequent steps.

When a result of step 410 is affirmative (i.e. the smart garment is worn on a human body), the process proceeds to step 415, in which the health care device operates in a normal mode. When the result of step 410 is negative (the smart garment is not worn on a human body), step 420 is performed to determine whether the smart garment 110 is worn on a human body within a predetermined period. A purpose of step 420 is to prevent an erroneous user operation from hindering the health care device to operate in a normal mode. For example, the erroneous user operation is an accidental user pull that disengages the metal contact LA. In response, the health care device detects the disengagement of the metal contact LA, and transmits a message to a remote device to request for a reconnection. Thus, instead of entering a low-power mode in which detection of the electrocardiography signal of a human is temporarily not executed, the health care device is ensured to persistently operate in a normal operating mode. In one embodiment, step 420 is optional. In one embodiment, for example, the predetermined period in step 420 is one minute.

When a result of step 420 is affirmative, the process iterates step 415. When the result of step 420 is negative, the power supplied to the wireless communication unit is disconnected so that the wireless communication unit enters a low-power mode to reduce power consumption, as shown in step 425.

In step 430, it is continually determined whether a user tap is detected. Details of detecting the user tap may be referred from associated descriptions above. In one embodiment, when the health care device is under a low-power mode, a user may tap the health care device for several times if the user wishes to send the detection/determination result of the health care device to a cell phone. As the activity detection unit 225 detects the user tap, the processing unit 210 turns on the power supply to the wireless communication unit 235 in step 440, so as to transmit health data to the cell phone via the wireless communication unit 235.

In step 445, the health care device determines whether the data is completely transmitted. The transmission process is continued if the data is not yet completely transmitted, or else step 425 is iterated to disconnect the power supplied to the wireless communication unit to enter a low-power mode.

Figure 5:
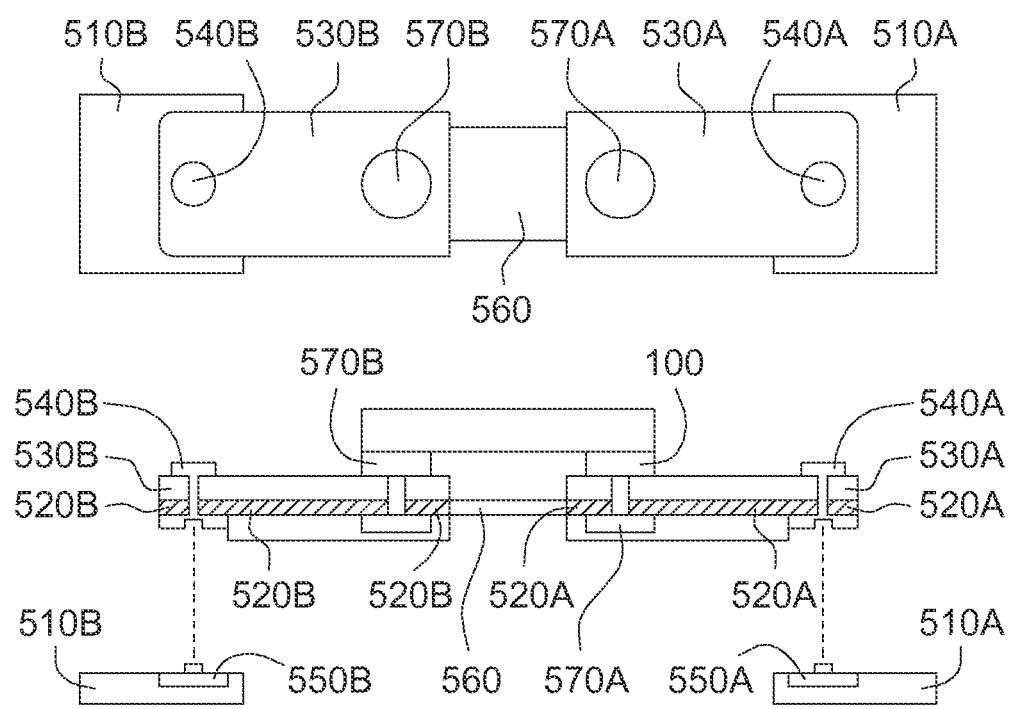
FIG. 5 shows a health care device being fixedly attached to a human body via an electrode patch according another embodiment of the disclosure.

FIG. 5 shows a health care device being fixedly attached to a human body via an electrode patch according to an alternative embodiment. As shown in FIG. 5, the electrode patch includes conductive adhesives 510A and 510B, conductive layers 520A and 520B, fabrics 530A and 530B, fastening units 540A and 540B, fastening units 550A and 550B, an insulation layer 560, and magnetic snaps 570A and 570B.

The conductive adhesives 510A and 510B are in contact with a human body to transmit a human physiological signal to the health care device 100. The fabrics 530A and 530B may envelop the conductive layers 520A and 520B. The fastening units (e.g., female buckles) 540A and 540B of the fabrics 530A and 530B may be fastened to the fastening units (e.g., male buckles) 550A and 550B of the conductive adhesives 510A and 510B. Due to possibilities of coming into contact with a human body, the insulation layer 560 is made of an insulation material. The insulation layer 560 is non-water absorbent, so as to prevent absorption of user perspiration that may cause an error in the measurement in the electrocardiography. The health care device 100 may be attracted and engaged by the magnetic snaps 570A and 570B, as shown in FIGS. 1A and 1B.

With the above embodiments, it is demonstrated that the health care device of the disclosure is capable of switching to an appropriate mode according to different application situations to minimize necessary power consumption.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A power management method for a health care device, the health care device comprising a leads-off detection unit, a processing unit and an activity detection unit, the power management method comprising:
    determining by the leads-off detection unit whether a smart garment is in contact with a user body;
    operating the health care device in a normal operating mode when it is determined that the smart garment is in contact with the user body;
    deactivating a wireless communication unit to operate the health care device in a low-power mode when the leads-off detection unit determines that the smart garment is not in contact with the user body within a predetermined period; and
    when the health care device is in the low-power mode, detecting by the activity detection unit whether the health care device is tapped to determine whether to transmit user health data detected by the health care device to a user device.

2. The power management method according to claim 1, wherein the leads-off detection unit detects respective potentials of a plurality of metal contacts of the health care device to determine whether the smart garment is in contact with the user body.

3. The power management method according to claim 1, wherein the health care device further comprises:
    a power activation detection unit, for detecting a magnetic field change to determine whether the health care device is fixedly attached to the smart garment.

4. A health care device, comprising:
    a processing unit;
    an activity detection unit, coupled to the processing unit;
    a power module, for powering the health care device;
    has been inserted, replacing
    a processing unit;
    a power module, for powering the health care device;

a physiological signal measurement unit, coupled to the processing unit, for measuring a user physiological signal;

a leads-off detection circuit, coupled to the processing unit, for detecting whether a smart garment fixedly attached to the health care device is in contact with a user body; and a wireless communication unit, coupled to the processing unit, for transmitting user health data measured by the health care device to a user device;

wherein, when the processing unit determines that the smart garment is in contact with the user body, the processing unit controls the health care device to operate in a normal operating mode; when the processing unit determines that the smart garment is not in contact with the user body within a predetermined period, the processing unit deactivates the wireless communication unit to control the health care device to operate in a low-power mode wherein, when the health care device operates in the low-power mode, the processing unit activates the wireless communication unit and transmits the user health data to the user device when the activity detection unit detects that the health care device is tapped.

5. The health care device according to claim 4, further comprising:

a plurality of metal contacts, coupled to the leads-off detection circuit;

wherein, the leads-off detection circuit detects respective potentials of the metal contacts and transmits the potentials of the metal contacts to the processing unit, and the processing unit accordingly determines whether the smart garment is in contact with the user body.

6. The health care device according to claim 5, further comprising:

a charging detection contact, for detecting whether the health care device is placed at an external charging module;

wherein, when the health care device is placed at the external charging module, the health care device charges the power module via the metal contacts.

7. The health care device according to claim 4, further comprising:

a power activation detection unit, for detecting a magnetic field change to determine whether the health care device is fixedly attached to the smart garment.

* * * * *